United States Patent [19]

Kurihara et al.

[11] Patent Number: 5,100,659
[45] Date of Patent: Mar. 31, 1992

[54] WHITE COLORED DEODORIZER AND PROCESS FOR PRODUCING THE SAME

[75] Inventors: Tokumitsu Kurihara; Tatsuo Saito; Hidefumi Harada, all of Yamaguchi, Japan

[73] Assignee: Titan Kogyo Kabushiki Kaisha, Ube, Japan

[21] Appl. No.: 539,322

[22] Filed: Jun. 14, 1990

Related U.S. Application Data

[63] Continuation of Ser. No. 222,959, Jul. 22, 1988, abandoned.

[51] Int. Cl.⁵ .............................................. A61L 9/01
[52] U.S. Cl. .................................... 424/76.1; 423/593; 423/610; 424/76.5; 424/76.6; 424/76.9
[58] Field of Search .................. 424/76.1, 76.3, 76.5, 424/76.6, 76.7, 65, 76.9; 106/8.8, 449; 423/610, 593

[56] References Cited

U.S. PATENT DOCUMENTS

| | | | |
|---|---|---|---|
| 2,350,047 | 9/1941 | Klarmann et al. | 424/68 |
| 3,202,524 | 8/1965 | Richmond | 106/449 |
| 3,383,231 | 5/1968 | Allan | 106/430 |
| 3,418,147 | 12/1968 | Fields | 106/430 |
| 3,961,037 | 6/1976 | Davies et al. | 423/656 |
| 4,088,736 | 5/1978 | Courty et al. | 423/230 |
| 4,128,630 | 12/1978 | Hayashi et al. | 424/69 |
| 4,187,282 | 2/1980 | Matsuda et al. | 423/244 |
| 4,297,233 | 10/1981 | Gualandi | 252/259.5 |
| 4,371,507 | 2/1983 | Farha, Jr. et al. | 423/230 |
| 4,492,769 | 1/1985 | Blanchard et al. | 502/262 |
| 4,537,873 | 8/1985 | Kato et al. | 502/350 |
| 4,777,034 | 10/1988 | Oliver et al. | 424/65 |

FOREIGN PATENT DOCUMENTS

| | | | |
|---|---|---|---|
| 0203022 | 12/1982 | Japan | 502/350 |
| 0210848 | 12/1983 | Japan | 502/343 |
| 141400 | 2/1986 | Japan . | |
| 1093835 | 5/1986 | Japan . | |
| 2179466 | 8/1987 | Japan | 424/76.1 |
| WO81/01643 | 6/1981 | PCT Int'l Appl. . | |

Primary Examiner—Ellis P. Robinson
Assistant Examiner—Archene Turner
Attorney, Agent, or Firm—Fitch, Even, Tabin & Flannery

[57] ABSTRACT

A white colored deodorizer comprising titanium oxide and at least one alkaline earth metal oxide selected from the group consisting of magnesium oxide and calcium oxide and a method for preparation of it are disclosed.

5 Claims, No Drawings

WHITE COLORED DEODORIZER AND PROCESS FOR PRODUCING THE SAME

This application is a continuation of application Ser. No. 222,959 filed July 22, 1988, now abandoned.

BACKGROUND OF THE INVENTION

The present invention relates to an agent for reducing the levels of odorous gases such as ammonia, mercaptans, amines and aldehydes. More specifically, the present invention relates to a novel deodorizer in white particulate form that contains as main ingredients titanium dioxide and at least one alkaline earth metal oxide selected from the group consisting of magnesium oxide, calcium oxide and mixtures thereof and which has very good adsorption characteristics.

Hydrogen sulfide, ammonia, mercaptans, amines, aldehydes and other odorous gases that are generated in daily life have caused an increasing amount of social concern about the deleterious effects they have on the biosphere and environment. In response to these concerns, a variety of deodorizers that are capable of reducing the target odorous gases have been proposed and put to practical use. Deodorizers for use in daily life have to satisfy the following minimal requirements:
(1) they must be capable of efficient reduction of the levels of hydrogen sulfide, ammonia, mercaptans, amines, aldehydes and other odorous gases that are generated in daily life;
(2) they must be safe to use;
(3) they must be easy to handle;
(4) they must be inexpensive; and
(5) they must offer a feeling of cleanliness.

However, none of the conventional deodorizers satisfy all of these requirements, nor do the most recently developed products. Activated carbon which is the most popular deodorizer in use today is highly effective in reducing mercaptans and amines but is not equally effective against hydrogen sulfide and ammonia which are typical of the odorous gases that are generated in daily life. In an attempt to solve this problem, a product has been developed that has an acid, an alkali or a certain halide supported on activated carbon. However, because of the use of an acid or alkali, this product requires very careful handling to avoid any danger to humans and hence is not suitable for daily use. Furthermore, the inherent black color of activated carbon limits the scope of use of deodorizers based on activated carbon.

Iron sulfate ($FeSO_4$) having L-ascorbic acid bound thereto is effective against basic odorous gases such as ammonia and amines but is little effective in reducing hydrogen sulfide, mercaptans and aldehydes. Furthermore, this product dissolves in water and hence is not suitable for the purpose of deodorizing wet gases.

Deodorizers classified as chemical odor modifiers are also available but many of them have strong acidity or alkalinity and the kinds of odorous gases that can be effectively controlled by these odor modifiers are limited. In addition, such deodorizers are sensitive to moisture and/or a dry atmosphere.

Organic deodorizers have low heat resistance, are difficult to process, and are expensive.

SUMMARY OF THE INVENTION

It is accordingly an object of the present invention to provide a novel deodorizer that is highly effective in reducing odorous gases generated in daily life such as ammonia, mercaptans, amines and aldehydes and which are safe and easy to handle.

This object of the present invention can be attained by a white colored deodorizer which is a white fine powder comprising coagulated particles of titanium dioxide and at least one alkaline earth metal oxide selected from the group consisting of magnesium oxide, calcium oxide and a mixture thereof.

According to another aspect of the present invention, the white colored deodorizer further contains zinc oxide.

DETAILED DESCRIPTION OF THE INVENTION

The deodorizer according to the first aspect of the present invention may be produced by the following procedures. A mixed aqueous solution of a water-soluble titanium compound and at least one alkaline earth metal compound selected from the group consisting of water-soluble magnesium compounds, water-soluble calcium compounds and mixtures thereof is mixed with an alkaline aqueous solution by simultaneous addition into a certain medium in such a way that the combined solution will have a final pH of at least 6, preferably 6–12, thereby forming a white precipitate in the combined solution that is composed of titanium dioxide, at least one alkaline earth metal oxide selected from the group consisting of magnesium oxide (MgO), calcium oxide (CaO) and mixtures thereof, and bound water ($H_2O$). In the next step, the precipitate is separated from the combined solution and dried.

Examples of the water-soluble titanium compounds that can be used as a starting material for the production of the deodorizer of the present invention include titanium sulfate, titanyl sulfate, titanium chloride and titanium nitrate. Examples of suitable water-soluble magnesium compounds include magnesium sulfate, magnesium, magnesium nitrate and magnesium acetate. Illustrative water-soluble calcium compounds include calcium chloride and calcium nitrate.

The alkaline aqueous solution used for neturalizing the mixed aqueous solution may be selected from among aqueous solutions of sodium hydroxide, potassium hydroxide, magnesium hydroxide, calcium hydroxide, barium hydroxide, ammonia, etc. If the mixed aqueous solution contains a sulfate salt, aqueous solutions of calcium hydroxide and barium hydroxide are not desirably used since they will produce water-insoluble salts.

The water-soluble titanium compound and at least one alkaline earth metal compound selected from the group consisting of water-soluble magnesium compounds, water-soluble calcium compounds and mixtures thereof are mixed in such proportions that the molar ratio of $TiO_2$ to at least one alkaline earth metal oxide selected from the group consisting of MgO, CaO and mixtures thereof is within the range of 1:9 to 9:1, preferably from 4:6 to 8:2. If the molar ratio of $TiO_2$ to said alkaline earth metal oxide is smaller than 1:9 or greater than 9:1, the fine powder prepared from the resulting precipitate will display absorption characteristics similar to either pure said alkaline earth metal oxide or pure titanium dioxide. These characteristics are substantially inferior to those of the fine powder obtained in accordance with the compositional range specified by the present invention.

Titanic acid starts to precipitate at a pH of about 1 or higher but neither magnesium hydroxide nor calcium hydroxide will form a precipitate unless the pH is at least 9-10. However, if the molar ratio of $TiO_2$ to said alkaline earth metal oxide in the mixed aqueous solution is greater than unity, substantially 100% precipitation of magnesium at least one alkaline earth metal hydroxy compound selected from the group consisting of hydroxide, calcium hydroxide and mixtures thereof together with titanic acid can be accomplished by increasing the pH of the mixed aqueous solution above 6.

If the combined solution has a pH of 12 or above, a precipitate will form that contains residual alkali or alkaline earth metal ions and the finally obtained white colored deodorizer will have an undesirably high pH.

For the purposes of the present invention, it is essential that the mixed aqueous solution and the aqueous alkaline solution be mixed together in such a way that the resulting combined solution will keep its pH of at least 6. If the alkaline aqueous solution is added to the mixed aqueous solution gradually over a certain period of time until the combined solution has a final pH of at least 6, preferably between 6 and 12, and the combined solution does not keep its pH between 6 and 12 during the alkaline solution is added, magnesium hydroxide or calcium hydroxide will not precipitate together with titanic acid and the finally obtained product will not have the intended composition. The concentrations of the water-soluble titanium compound and at least one alkaline earth metal compound selected from water-soluble magnesium compounds, water-soluble magnesium compounds and mixtures thereof in the mixed aqueous solution are not limited to any particular values.

When the mixed aqueous solution and the alkaline aqueous solution are mixed together to form a precipitate composed of $TiO_2$, and at least one alkaline earth metal oxide selected from the group consisting of MgO and CaO, a temperature in the range of 20°-80° C. may be employed, with the range of 40°-60° C. being preferred.

After the precipitate has been filtered and washed, it may be dried at a temperature in the range of 100°-350° C., preferably 120°-250° C. The deodorizer of the present invention which contains as essential ingredients $TiO_2$ and at least one alkaline earth metal oxide selected from the group consisting of MgO, CaO and mixtures thereof will maintain satisfactory adsorption characteristics even if it is heated up to 400° C.

A deodorizer according to the second aspect of the present invention may be produced by the following procedures. A mixed solution of a water-soluble titanium compound, a water-soluble zinc compound, and at least one alkaline earth metal compound selected from the group consisting of water-soluble magnesium compounds, water-soluble calcium compounds and mixtures thereof is mixed with an ammonia gas or aqueous solution in such a way that the combined solution will have a final pH of 6-12, preferably 7-9, thereby forming a white precipitate in the combined solution that is composed of $TiO_2$, ZnO, at least one alkaline earth metal oxide selected from the group consisting of MgO, CaO and mixtures thereof. In the next step, the precipitate is separated from the combined solution and dried.

Examples of the water-soluble zinc compound that can be used in the present invention in its second aspect include zinc sulfate, zinc chloride, zinc nitrate and zinc acetate. As for the water-soluble titanium compound, water-soluble magnesium compound, water-soluble calcium compound and the alkaline aqueous solution used to neutralize the mixed aqueous solution, reference should be made to the pertinent portion of the foregoing description of the first aspect of the present invention. If a deodorizer containing calcium oxide is to be produced, it is not preferable for the mixed aqueous solution to contain a sulfuric acid salt of titanium, zinc or magnesium since they will produce calcium sulfate which is insoluble in the mixed aqueous solution.

The water-soluble titanium compound, the water-soluble zinc compound and at least one alkaline earth metal compound selected from the group consisting of water-soluble magnesium compounds, water-soluble calcium compounds and mixtures thereof are mixed together in respective proportions of 10-90 mol % (preferably 30-70 mol %), 10-90 mol % (preferably 30-70 mol %) and 0.1-50 mol % (preferably 0.5-30 mol %). If at least one of these ingredients is used in an amount smaller than the prescribed lower limit, the desired effect is not attained by mixing the respective ingredients. If either one of these ingredients is used in an amount greater than the prescribed higher limit, the fine powder prepared from the resulting precipitate will display absorption characteristics substantially equal to either pure $TiO_2$, or pure ZnO or pure said alkaline earth metal oxide. These characteristics are found to be substantially inferior to those of the fine powder obtained in accordance with the compositional range specified by the present invention.

For the purposes of the present invention, it is essential that the mixed aqueous solution consisting of the water-soluble titanium compound, water-soluble zinc compound, and at least one alkaline earth metal compound selected from the group consisting of water-soluble magnesium compounds, water-soluble calcium compounds and mixtures thereof should be mixed with the aqueous alkaline solution in such a way that the resulting combined solution will have a final pH in the range of 6-12.

At pHs below 6 or above 12, zinc hydroxide has high solubility in aqueous solutions and the efficiency of its precipitation is decreased. On the other hand, magnesium hydroxide and calcium hydroxide have high solubility in aqueous solutions at pHs in the range of 9-10 and the efficiency of their precipitation is decreased. In the present invention which involves the use of a mixed aqueous solution containing the water-soluble titanium compound, zinc hydroxide, magnesium hydroxide and calcium hydroxide will co-precipitate with titanic acid to form hydroxides in the pH range of 6-12, the efficiency of precipitation is high enough to minimize the otherwise occurring deviation from the intended composition of the combined solution.

If the aqueous alkaline solution is slowly added to the mixed aqueous solution, or the mixed solution is slowly added to the aqueous alkaline solution, until the resulting combined solution has a final pH of 6-12, titanic acid, zinc hydroxide, magnesium hydroxide and calcium hydroxide, which have different optimal pH regions for precipitation, will individually form separate particles and the powder that is obtained by drying them will be a mixture of pure $TiO_2$, ZnO, and MgO and/or CaO, which does not have superior characteristics. The concentrations of the water-soluble titanium compound, the water-soluble zinc compound and at least one alkaline earth metal compound selected from the group consisting of water-soluble magnesium compounds, water-soluble calcium compounds and mixtures thereof in the mixed aqueous solution are not limited to any particular values.

When the mixed aqueous solution and the alkaline aqueous solution are mixed together to form a precipitate composed of $TiO_2$, ZnO, MgO and/or CaO, a temperature in the range of 20°-80° C. may be employed, with the range of 40°-60° C. being preferred. After the precipitate has been filtered and washed, it may satisfactorily be dried at a temperature over the wide range of 100°-350° C., with the range of 150°-220° C. being preferred.

The deodorizer of the present invention which is based on the combination of $TiO_2$, ZnO and at least one alkaline earth metal oxide selected from among MgO, CaO and mixtures thereof will experience a slight change in its adsorption characteristics if it is heated above 220° C. but it is sufficiently heat stable to maintain good characteristics even if it is heated up to about 400° C.

The white-colored deodorizer of the present invention which is based on the combination of $TiO_2$, at least one alkaline earth metal oxide selected from among MgO, CaO and mixtures thereof, and optionally ZnO is capable of efficient reduction in the levels of hydrogen sulfide, ammonia, amines and other odorous gases that are generated in daily life. In addition, this deodorizer is safe to use since the $TiO_2$, ZnO (optional) said alkaline earth metal oxide that are incorporated are nontoxic. Furthermore, the deodorizer is in a fine particulate form and can be readily supported on a carrier such as paper or other sheet materials. The deodorizer is thermally stable up to about 400° C. and can be worked into conventional plastics. In addition to the high potential of its industrial utility, the deodorizer of the present invention which is white in color is also suitable for use in cosmetics, sanitary products and disposable diapers.

The following examples are provided for the purpose of further illustrating the present invention but are not to be taken as limiting the scope thereof.

EXAMPLE 1

A 5-l beaker was charged with 1 l of pure water, which was heated at 60° C. with stirring. A mixed aqueous solution (2 l) of titanium sulfate (120 g as $TiO_2$) and magnesium sulfate (20 g as MgO) and an aqueous ammonia solution were simultaneously added dropwise to the pure water in the beaker over a period of 30 minutes with care being taken to ensure that the pH of the combined solution remained at 8. The resulting product was filtered, washed and dried at 200° C. for 3 hours to produced a white deodorizer of the $TiO_2$-MgO-$H_2O$ system within the scope of the present invention. An X-ray diffraction analysis showed that this white deodorizer was amorphous.

The ability of this white deodorizer to adsorb odorous gases (i.e., hydrogen sulfide, ammonia, trimethylamine and ethyl mercaptan) was investigated by the following method. The white powder of the deodorizer (100 mg) was put into a glass vial having an inner capacity of 120 ml. After closing the vial with a rubber stopper, predetermined amounts of certain odorous gases were injected into the vial with a microsyringe. Two hours after the gas injection, the air in the vial was sampled with a microsyringe and the concentrations of the odorous gases in it were measured by gas chromatography. The results are shown in Table 1.

EXAMPLE 2

A white deodorizer of the $TiO_2$-MgO-$H_2O$ system was prepared by repeating the procedures of Example 1 except that a mixed aqueous solution of titanium sulfate (80 g as $TiO_2$) and magnesium sulfate (40 g as MgO) was used. The adsorption characteristics of the prepared deodorizer for various odorous gases are shown in Table 1.

EXAMPLE 3

A white deodorizer of the $TiO_2$-CaO-$H_2O$ system was prepared by repeating the procedures of Example 1 except that a mixed aqueous solution of titanium chloride (120 g as $TiO_2$) and calcium chloride (28 g as CaO) was used. The adsorption characteristics of the prepared deodorizer for various odorous gases are shown in Table 1.

EXAMPLE 4

A white deodorizer of the $TiO_2$-CaO-$H_2O$ system was prepared by repeating the procedures of Example 1 except that a mixed aqueous solution of titanium chloride (80 g as $TiO_2$) and calcium chloride (56 g as CaO) was used. The adsorption characteristics of the prepared deodorizer for various odorous gases are shown in Table 1.

EXAMPLE 5

A white deodorizer of the $TiO_2$-MgO-CaO-$H_2O$ system was prepared by repeating the procedures of Example 1 except that a mixed aqueous solution of titanium chloride (80 g as $TiO_2$), magnesium chloride (20 g as MgO) and calcium chloride (28 g as CaO) was used. The adsorption characteristics of the prepared deodorizer for various odorous gases are shown in Table 1.

EXAMPLE 6

A 5-l beaker was charged with 1 l of pure water, which was heated at 60° C. with stirring. A mixed aqueous solution (2 l) of titanium sulfate (79.1 g as $TiO_2$), zinc sulfate (65.9 g as ZnO) and magnesium sulfate (8.1 g as MgO) and an aqueous ammonia solution were simultaneously added dropwise to the pure water in the beaker over a period of 30 minutes with care being taken to ensure that the pH of the combined solution remained at 8. The resulting product was filtered, washed and dried at 200° C. for 3 hours to produce a white deodorizer of the $TiO_2$-ZnO-MgO system within the scope of the present invention. X-ray diffraction analysis showed that this white deodorizer was amorphous.

The adsorption characteristics of the prepared deodorizer for various odorous gases are shown in Table 1.

EXAMPLE 7

A white deodorizer of the $TiO_2$-ZnO-MgO system was prepared by repeating the procedures of Example 6 except that the amounts of $TiO_2$, ZnO and MgO in 2 l of the mixed aqueous solution of titanium sulfate, zinc sulfate and magnesium sulfate were changed to 61.5 g, 51.3 g and 33.6 g, respectively. The adsorption characteristics of the prepared deodorizer for various odorous gases are shown in Table 1.

EXAMPLE 8

A white deodorizer of the $TiO_2$-ZnO-CaO system was prepared by repeating the procedures of Example 6 except that the amounts of $TiO_2$, ZnO and CaO in 2 l of the mixed aqueous solution of titanium chloride, zinc chloride and calcium chloride were changed to 79.1 g, 65.9 g and 12.1 g, respectively. The adsorption characteristics of the prepared deodorizer for various odorous gases are shown in Table 1.

EXAMPLE 9

A white deodorizer of the $TiO_2$-ZnO-CaO system was prepared by repeating the procedures of Example 6 except that the amounts of $TiO_2$, ZnO and CaO in 2 l of the mixed aqueous solution of titanium chloride, zinc chloride and calcium chloride were changed to 61.5 g, 51.3 g and 24.2 g, respectively. The adsorption characteristics of the prepared deodorizer for various odorous gases are shown in Table 1.

EXAMPLE 10

A white deodorizer of the $TiO_2$-ZnO-MgO-CaO system was prepared by repeating the procedures of Example 6 except that the amounts of $TiO_2$, ZnO, MgO and CaO in 2 l of the mixed aqueous solution of titanium chloride, zinc chloride, magnesium chloride and calcium chloride were changed to 61.5 g, 51.3 g, 16.8 g and 12.1 g, respectively. The adsorption characteristics of the prepared deodorizer for various odorous gases are shown in Table 1.

COMPARATIVE EXAMPLE 2

A zinc oxide powder was prepared by repeating the procedures of Comparative Example 1 except that the aqueous solution of titanium sulfate was replaced by an aqueous solution of zinc sulfate (81.4 g as ZnO). The adsorption characteristics of the prepared powder for various odorous gases are shown in Table 1.

COMPARATIVE EXAMPLE 3

A magnesium oxide powder was prepared by repeating the procedures of Comparative Example 1 except that the aqueous solution of titanium sulfate was replaced by 1 l of an aqueous solution of magnesium sulfate (80 g as MgO) and that the neutralization pH was changed from 7.5 to 11. The adsorption characteristics of the prepared powder for various odorous gases are shown in Table 1.

COMPARATIVE EXAMPLE 4

A calcium oxide powder was prepared by repeating the procedures of Comparative Example 1 except that the aqueous solution of titanium sulfate was replaced by 1 l of an aqueous solution of calcium chloride (56 g as CaO) and that the neutralization pH was changed from 7.5 to 11. The adsorption characteristics of the prepared powder for various odorous gases are shown in Table 1.

COMPARATIVE EXAMPLE 5

The adsorption characteristics of a commercial grade of activated carbon (specific surface area = 1,200 $m^2/g$) for various odorous gases are shown in Table 1.

TABLE 1

| Run No. | Composition (molar ratio) | Nature | Gas concentrations (ppm) after 2 hours of adsorption | | | |
|---|---|---|---|---|---|---|
| | | | hydrogen sulfide (10,000*) | ammonia (10,000*) | trimethyl-amide (10,000*) | ethyl mercaptan (5,000*) |
| Ex. | | | | | | |
| 1 | $TiO_2$:MgO = 75:25 | amorphous | 0 | 80 | 100 | 200 |
| 2 | $TiO_2$:MgO = 50:50 | amorphous | 0 | 100 | 300 | 500 |
| 3 | $TiO_2$:CaO = 75:25 | amorphous | 0 | 300 | 200 | 200 |
| 4 | $TiO_2$:CaO = 50:50 | amorphous | 0 | 350 | 400 | 900 |
| 5 | $TiO_2$:MgO:CaO = 50:25:25 | amorphous | 0 | 200 | 200 | 500 |
| 6 | $TiO_2$:ZnO:MgO = 5:4:1 | amorphous | 0 | 65 | 10 | 0.5 |
| 7 | $TiO_2$:ZnO:MgO = 4:3:3 | amorphous | 0 | 30 | 30 | 0.7 |
| 8 | $TiO_2$:ZnO:CaO = 5:4:1 | amorphous | 0 | 15 | 10 | 0.3 |
| 9 | $TiO_2$:ZnO:CaO = 4:3:3 | amorphous | 0 | 35 | 20 | 0.4 |
| 10 | $TiO_2$:ZnO:MgO:CaO = 4:3:1.5:1.5 | amorphous | 0 | 30 | 20 | 0.4 |
| Comp. Ex. | | | | | | |
| 1 | titanic acid | | 8,000 | 830 | 3,000 | 5,000 |
| 2 | zinc oxide | | 2.5 | 5,800 | 8,000 | 3,500 |
| 3 | magnesium oxide | | 1.0 | 8,000 | 9,000 | 5,000 |
| 4 | calcium oxide | | 20 | 9,000 | 9,000 | 5,000 |
| 5 | activated carbon | | 2.5 | 550 | 0 | 0.6 |

*Initial concentrations in ppm

COMPARATIVE EXAMPLE 1

A 5-l beaker was charged with 1 l of pure water, which was heated at 60° C. with stirring. An aqueous solution (1 l) of titanium sulfate (79.9 g as $TiO_2$) and an aqueous ammonia solution were simultaneously added dropwise to the pure water in the beaker with care being taken to ensure that the pH of the combined solution remained at 7.5. The resulting plrecipitate was filtered, washed and dried at 200° C. for 3 hours to obtain a titanic acid powder. The adsorption characteristics of this titanic acid powder for various odorous gases are shown in Table 1.

What is claimed is:

1. A process for producing a white colored deodorizer consisting essentially of titanium dioxide and at least one alkaline earth metal oxide selected from the group consisting of MgO, CaO and mixtures thereof, where the molar ratio of $TiO_2$ to said alkaline earth metal oxide is in the range of from 1:9 to 9:1, the process consisting essentially of the following steps:

combining an aqueous alkaline solution with a mixed aqueous solution containing a water-soluble titanium compound and at least one alkaline earth metal compound selected from the group consisting of water-soluble magnesium compounds, water-soluble calcium compounds and mixtures thereof, said combining step being performed by simultaneous addition of the two solutions in such a way that the combined solution will keep its pH in the range of 6 to 12 and said combining step is performed at a temperature of 20° C. to 80° C. to form a precipitate;

separating the precipitate from the combined solution; and drying the separated precipitate at 120° C. to 350° C. to form a white fine powder consisting essentially of $TiO_2$, and at least one alkaline earth metal oxide selected from the group consisting of MgO, CaO and mixtures thereof.

2. A process for producing a white colored deodorizer consisting essentially of titanium dioxide, ZnO and at least one alkaline earth metal oxide selected from the group consisting of MgO, CaO and mixtures thereof, where the molar ratio of $TiO_2$ and ZnO to said alkaline earth metal oxide is in the range of from 1:9 to 9:1, the process consisting essentially of the following steps:

combining an aqueous alkaline solution with a mixed aqueous solution containing a water-soluble titanium compound, a water-soluble zinc compound and at least one alkaline earth metal compound selected from the group consisting of water-soluble magnesium compounds, water-soluble calcium compounds and mixtures thereof, said combining step being performed by simultaneous addition of the two solutions in such a way that the combined solution will have a final pH in the range of 6 to 12 and said combining step is performed at a temperature of 20° C. to 80° C. to form a precipitate;

separating the precipitate from the combined solution; and drying the separated precipitate at 120° C. to 350° C. to form said white fine powder.

3. A process according to claim 1, wherein the molar ratio of $TiO_2$ to said alkaline earth metal oxide is in the range of from 4:6 to 8:2.

4. A process according to claim 2, wherein the proportions of $TiO_2$, ZnO and said alkaline earth metal oxide are in the ranges of 30 to 70 mol %, 30 to 70 mol % and 0.5 to 30 mol %, respectively.

5. A process according to claim 4 wherein the reaction for forming said precipitate is carried out at a temperature of 20° C. to 80° C., and the resulting precipitate is dried at a temperature of 120° C. to 350° C.

* * * * *

UNITED STATES PATENT AND TRADEMARK OFFICE
CERTIFICATE OF CORRECTION

PATENT NO.  :   5,100,659

DATED       :   March 31, 1992

INVENTOR(S) :   Kurihara et al.

It is certified that error appears in the above-identified patent and that said Letters Patent is hereby corrected as shown below:

```
     Column 3, line 24, delete "during" and insert --when--.
     Column 3, line 31, delete "magnesium" and insert --calcium--.
     Column 3, line 60, after "ZnO" insert --and--.
     Column 4, line 46, before "which" insert --(--.
     Column 5, line 43, change "5-1" to --5-1-- (liter) and change
"1 1" to --1 1-- (liter).
     Column 5, line 45, change "(2 1)" to --(2 1)-- (liter).
     Column 5, line 49, change "minutes-with" to --minutes with--.
     Column 6, line 41, change "5-1" to --5-1-- (liter) and change
"1-1" to --1-1-- (liter).
     Column 6, line 43, change "(2-1)" to --(2-1)-- (liter).
     Column 6, line 63, change "2 1" to --2 1-- (liter).
     Column 7, line 5, change "2 1" to --2 1-- (liter).
     Column 7, line 15, change "2 1" to --2 1-- (liter).
     Column 7, line 26, change "2 1" to --2 1-- (liter).
     Column 7, line 58, change "5 1" to --5 1-- (liter) and change
"1 1" to --1 1-- (liter).
     Column 7, line 60, change "1 1" to --1 1-- (liter).
     Column 8, line 14, change "1 1" to --1 1-- (liter).
```

UNITED STATES PATENT AND TRADEMARK OFFICE
CERTIFICATE OF CORRECTION

PATENT NO. : 5,100,659

DATED : March 31, 1992

INVENTOR(S) : Kurihara et al.

It is certified that error appears in the above-identified patent and that said Letters Patent is hereby corrected as shown below:

Column 8, line 24, change "1 l" to --1 l--. (liter).

Signed and Sealed this

Tenth Day of August, 1993

Attest:

MICHAEL K. KIRK

*Attesting Officer*    Acting Commissioner of Patents and Trademarks